US00PP10140P

United States Patent [19]

Henny

[11] Patent Number: Plant 10,140

[45] Date of Patent: Dec. 2, 1997

[54] AGLAONEMA PLANT NAMED '39303'

[75] Inventor: Richard J. Henny, Tavares, Fla.

[73] Assignee: Florida Foundation Seed Producers, Inc., Greenwood, Fla.

[21] Appl. No.: 636,863

[22] Filed: Apr. 23, 1996

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 6,842 6/1989 Brown ..... Plt./88

*Primary Examiner*—James R. Feyrer
*Assistant Examiner*—Kent L. Bell
*Attorney, Agent, or Firm*—John H. Vynalek; Frank B. Robb

[57] ABSTRACT

There is disclosed a representative plant of Aglaonema designated '39303' which is one displaying variegated foliage consisting of three colors on the upper leaf surface, comprising dark green leaf margins that connect to a lighter grey-colored central area in an irregular pattern that often overlaps to produce small irregular patches of a third distinct foliar color of grey-green; leaf midrib and major lateral veins having showy greyed-yellow tint that highlights the other leaf colors; and a white petiole which accents the leaf coloration.

1 Drawing Sheet

BACKGROUND OF THE DISCLOSURE

This invention relates to Aglaonema Plants and, more particularly, to a cultivar thereof which is one of a series from a long, detailed program for developing such plants.

This program for the development of Aglaonema has been carried on in the vacinity of Apopka, Fla., and the particular seedling of this invention is a result of many crosses which is disclosed in an outline set forth below.

The detailed description of the plant enables the identification of the plant without regard to specific botanical statements, since the plant is clearly identifiable by reason of its certain peculiar differences as distinguished from prior existing Aglaonema.

I have chosen to designate the instant cultivar by the name '39303'. The '39303' plant was a selection from the progeny of '27708'×'1501' The parent '27708' was a selection from the cross of *A. commutatum* 'Tricolor'×*A. nitidum* 'Ernesto's Favorite'. The parent '1.501' was a selection from the cross of *A. commutatum* 'Tricolor' and A. 'Manila'. The plant was selected based on its unusual and distinctive expressions of foliar coloration and character, particularly its unusual three-color variegation on the upper leaf surface with a contrasting white petiole accenting such leaf coloration.

I determined that the plant '39303', discovered by me from the progeny of the above-stated cross, to be of commercial value due to its unusual and distinctive appearance. Asexual propagules of the plant '39303' were grown and observed for novelty and stability under green house conditions which closely approximate those generally used for commercial production at our facilities near Apopka, Fla. Measurements and values of the characteristic expressions from these specimens were recorded from which the plant can be botanically described and botanically distinguished.

Asexual propagation by stem cuttings and tissue culture was used to increase the number of plants for evaluation and has demonstrated the stability of the combination of characteristics of the new cultivar from generation to generation. These characteristics have been repeatedly observed and are determined to be basic characteristics of '39303', which in combination distinguish '39303' from other Aglaonema of the same general type such as Aglaonema 'Silver Queen' or any of those described in the following references:

Bailey, L. H. and E. Z., 1976, *Hortus Third*, Macmillan, New York.

Graf, A. B., 1978. Tropica—Color Cyclopedia of Exotic Plants and Trees. Roehrs Co., East Rutherford, N.J.

The observations, measurements and values describing '39303' may be summarized as including the following unique combinations:

The top surfaces of the leaves are an attractive and distinct variegation consisting of three colors; dark green leaf margins connecting to a lighter grey-green colored central area in an irregular pattern that often overlaps to create small irregular patches of a third distinct foliar color that is a darker shade of grey-green. The leaf midrib and major lateral veins have a showy greyed-yellow tint that is highlighted by the other leaf colors.

The petiole color is white and accents the leaf coloration, while the stem color is green but is generally not visible due to clasping nature of the petioles.

The plant '39303' has a natural good suckering habit which gives the finished plant a compact and full appearance.

DRAWINGS

The drawing comprises a front perspective color photograph of a plant of '39303,' with color being depicted as accurately as possible with illustrations of this type.

DETAILED DESCRIPTION

All color references below are measured against The Royal Horticultural Society Colour Chart. Colors are approximate as color depends on horticultural practices such as light level and fertilization rate, among others.

Origin: Aglaonema '27708'×Aglaonema '1501'.
Propagation: Asexual reproduction by either tissue culture or stem cuttings.
Classification: Aglaonema×'39303'.

PLANT DESCRIPTION

Overall size and growth habit: In an 15 cm standard pot, after approximately 7 months of growth under appropriate conditions beginning with a 16-week-old rooted liner obtained from tissue culture, '39303' will have an average plant canopy height of 27–30 cm and a canopy width of 35–45 cm. In the same time period the average height from the soil surface to the junction of the petioles with the most recently unfurled leaf would be 16–19 cm. Height from the soil surface to the tips of the uppermost leaves held upwards is 42–46 cm. The ultimate size of '39303', if planted in a sufficiently large container and grown under appropriate conditions, is unknown.

Stem: The stem color is varying shades of R.H.S. 146B-C (yellow-green) but is generally not visible due to the clasping nature of the petiole wings which surround the stem.

Petiole: The petiole color is R.H.S. 155A (white).

Leaf: The leaf is lanceolate, with an acuminate apex and an obtuse base which will sometimes be slightly oblique. The leaf margin is entire. The lamina on either side of the midrib tends to be of slightly unequal widths, resulting in a slight curving of the blade towards the narrower side.

*Dimensions.*—For the growing time and pot size indicated, the largest leaves will be approximately 9–10 cm wide and 28–30 cm long. Plant height, measured with the leaves held upright, will average 44 cm and plant spread from the leaf tips will be approximately 42 cm.

*Midrib.*—The midrib color is R.H.S. 160C-D (green-white) and tapers toward the apex. It protrudes prominently from the abaxial side of the leaf.

*Primary veins.*—The primary veins are sunken into the adaxial side and stand out from the abaxial of the leaf blade.

*Color and pattern.*—A mature leaf exhibits a central grey-green area (R.H.S. 191A-B) that extends out from each side of the midrib to cover slightly over half of the total laminar surface. Leaf margins are R.H.S. 139A (green) and intersect the lighter grey-green (R.H.S. 191A-B) colored central area along irregular borders that often overlap to create small distinct patches of a third color that is a darker grey-green (R.H.S. 189A). These distinct phenotypic leaf variegation patterns are due to the genotype $V^{mm}V^{ef}$ that produces leaves with two variegation patterns superimposed on each other. (see Henny, R. J. 1986. Single, locus, multiallelic inheritance of foliar variegation in Aglaonema. J. of Heredity 77:214–215; and Henny, R. J. 1992. Inheritance of the foliar variegation pattern from *Aglaonema nitidum* (jack) Kunth 'Ernesto's Favorite'. HortScience 27(3):274.) One pattern ($V^{mm}$) originated from Aglaonema 'Manila' and the other ($V^{ef}$) originated from A. 'Ernesto's Favorite'. The overlapping areas of the patterns produce segments with a third color.

These three leaf colors are highlighted by the greyed-yellow (R.H.S. 150C-D) leaf midrib. In the basal 2–4 cm of the midrib, the midrib coloration extends into the adjacent lamina areas up to 1 cm on each side. The coloration is more limited to the midrib as it progresses toward the apex. This coloration also extends into the major lateral veins in varying lengths but rarely exceeds one half the total length of any one vein.

Axillary breaks: The plant branches well, producing up to 4–6 or more lateral offshoots per main stem.

Blooming habit: Mature plants have been observed to flower in the spring in the greenhouse near Apopka, Fla.

Roots: Thick white roots with fine laterals.

I claim:

1. A new and distinct variety of Aglaonema as shown and described, characterized particularly as to novelty by the attractive and distinct variegated foliage consisting of three colors on the upper leaf surface, comprising dark green leaf margins that connect to a lighter grey-colored central area in an irregular pattern that often overlaps to produce small irregular patches of a third distinct foliar color of grey-green; leaf midrib and major lateral veins having showy greyed-yellow tint that highlights the other leaf colors; and a white petiole which accents the leaf coloration.

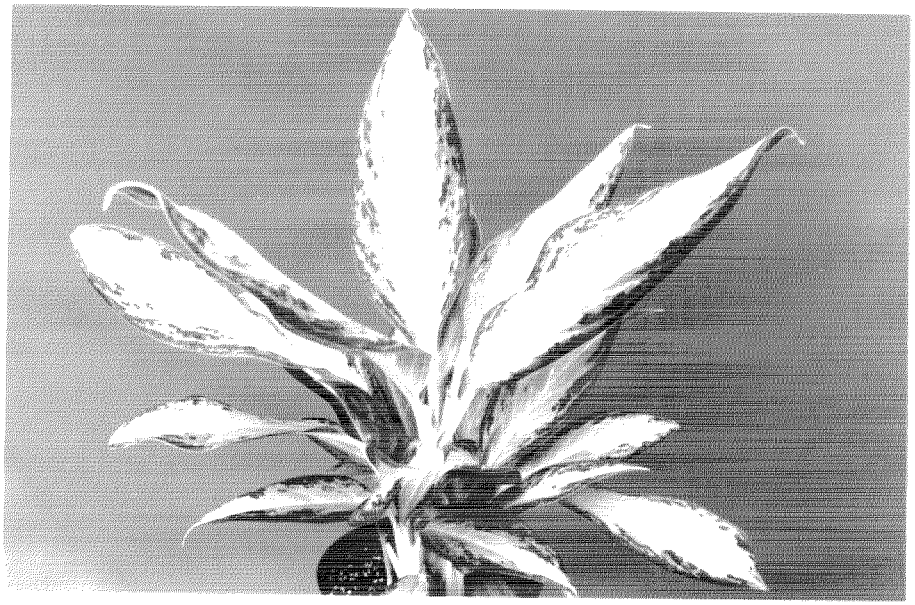

* * * * *